United States Patent [19]

Thunberg

[11] Patent Number: 5,079,380

[45] Date of Patent: Jan. 7, 1992

[54] ADIABATIC PROCESS FOR THE PREPARATION OF GLYCINONITRILE

[75] Inventor: Jon C. Thunberg, Milford, N.H.

[73] Assignee: W. R. Grace & Co.-Conn., New York, N.Y.

[21] Appl. No.: 527,391

[22] Filed: May 23, 1990

[51] Int. Cl.$^5$ .................... C07C 253/00; C07C 253/30
[52] U.S. Cl. .................... 558/346; 562/4 M; 562/575
[58] Field of Search .......................... 558/346

[56] References Cited

U.S. PATENT DOCUMENTS

| | | | |
|---|---|---|---|
| 3,167,582 | 1/1965 | Saunders et al. | 260/465.5 |
| 3,463,805 | 8/1969 | Morgan et al. | 260/465.5 |
| 3,515,742 | 6/1970 | Morgan et al. | 260/465.5 |
| 4,022,815 | 5/1977 | Schlecht et al. | 260/465.5 |
| 4,113,764 | 9/1978 | Distler et al. | 260/465.5 |
| 4,731,465 | 3/1988 | Shen et al. | 558/346 |

*Primary Examiner*—Joseph P. Brust
*Attorney, Agent, or Firm*—Kevin S. Lemack; William L. Baker

[57] ABSTRACT

A process for producing glycinonitrile under substantially adiabatic reaction conditions by reacting in a tubular reactor hydrogen cyanide, formaldehyde and ammonia. The excess ammonia is flashed off and the remaining solution volatiles are evaporated and condensed to product. The resulting glycinonitrile can be saponified to the alkali metal glycinate, from which glycine can be prepared.

15 Claims, 3 Drawing Sheets

ADIABATIC PROCESS FOR THE PREPARATION OF GLYCINONITRILE

BACKGROUND OF THE INVENTION

Glycinonitrile is an important intermediate in the preparation of alkali metal glycinates and glycine. As such, impurities in the glycinonitrile affect the purity and yield of the glycinates or glycine, often deleteriously.

Conventional glycinonitrile preparation requires essentially stoichiometric amounts of hydrogen cyanide and formaldehyde, but a minimum of about 200% excess ammonia. Several different routes for the preparation of glycinonitrile are known. For example, glycinonitrile can be prepared by the ammonolysis of glycolonitrile; by the reaction of an alkali metal cyanide, formaldehyde and an ammonium halide in the presence of acid; or by the reaction of chloracetonitrile and ammonia.

U.S. Pat. No. 3,167,582 discloses a process for the preparation of glycinonitrile by reacting hydrogen cyanide, formaldehyde and ammonia under critically controlled reaction conditions. Thus the mixing of the reactants, the mole ratio of the reactants, the temperature and pH of the reaction, and the residence time of the reactants within the reactor are parameters that are critically controlled so as to obtain glycinonitrile in high yields in a continuous manner.

The foregoing processes suffer from various drawbacks, such as low purity, resulting in low purity derivative products, and low product concentration, resulting in low production capacity and labor-intensive procedures.

A major drawback of present commercial processes for the preparation of glycine is the generation of waste crystal liquor. This liquor purges from the system the iminodiacetic acid (IDA) and other impurities which largely come from the impure glycinonitrile which is fed into the saponification step to produce the Na glycinate from which the glycine acid is derived. The substitution of $NH_3$ by cyanide and formaldehyde is never exclusively on a 1:1 molar basis to produce only glycinonitrile. Disubstitution always occurs to produce $HN(CH_2CH)_2$, or IDAN. Only by using massive excesses of $NH_3$ can this by-product formation be reduced to low levels. At a mole ratio of about 3:1 $NH_3$:($HCN+CH_2O$), the mole % conversion of ($HCN+CH_2O$) to glycinonitrile is 85-95%. Most of the other 5-15% goes to IDAN.

Because the nitrile is a solution, no purification by crystallization can occur. Typically the glycinonitrile solution is directly saponified in NaOH solution: the glycinonitrile to Na glycinate, and the IDAN to IDA-$Na_2$. The solution of Na glycinate and IDAN$a_2$ is subjected to crystallization at pH about 5-7, which is at or near the isoelectric point of glycine acid. At this pH the IDA exists as its very soluble mono Na salt (IDAHNa). The IDA must be purged from the system as a waste liquor containing glycine, IDAHNa, and other impurities, thereby generating a substantial waste which is responsible for the relatively low yields of glycine from the original HCN.

SUMMARY OF THE INVENTION

The problems of the prior art have been overcome by the instant invention, which provides an adiabatic process for the preparation of glycinonitrile which takes advantage of the heat of reaction generated by hydrogen cyanide, formaldehyde and ammonia.

In the process of this invention, the IDAN is still generated back in the tube reactor, but the IDAN and other impurities are non-volatile and can be separated from the volatile glycinonitrile by distillation. A wiped-film evaporator is preferred because of the very short contact time of such units. Because glycinonitrile is unstable, especially at increasing temperatures, typical batch distillation is inappropriate because of the large decomposition losses which would occur.

The solution produced from the distilled glycinonitrile is relatively pure and can be saponified to an alkali metal sodium glycinate solution which is also very pure. Because this alkali metal glycinate does not carry the heavy loading of impurities (especially IDAN$a_2$ in the case of sodium glycinate) into a subsequent glycine fractional crystallization scheme, very little crystal liquor purge is generated and much higher yields of glycine can be obtained.

In accordance with the preferred embodiment of the present invention, glycinonitrile is formed by the adiabatic conversion of hydrogen cyanide, formaldehyde and concentrated ammonia, followed by flash let-down of pressure, evaporation, and condensation of product. In a further embodiment of the present invention, the resulting distilled glycinonitrile can be saponified to an alkali metal glycinate.

It is therefore an object of the invention to provide a process for preparing glycinonitrile by the adiabatic reaction of hydrogen cyanide, ammonia and formaldehyde.

It is another object of the invention to provide a process for the preparation of glycinonitrile in highly purified solution form.

It is a further object of the invention to produce relatively pure alkalimetal glycinate from glycinonitrile.

These and other objects of the invention will become apparent to those skilled in the art from the following detailed description and examples.

DETAILED DESCRIPTION OF THE INVENTION

In the preferred embodiment of the present invention, the feedstocks to the process include concentrated ammonia, hydrogen cyanide, and formaldehyde (typically 38%-50%, preferably 44%) in a molar ratio of about 1.00 HCN:1.00-1.05 HCHO. In order to control the mole ratio of HCN:$CH_2O$ in the pilot unit, an acid stabilized mixture of hydrogen cyanide and formaldehyde can be used. This enables accurate weighing of the two components, as well as the use of only 2, rather than 3, pump heads. The reaction of the HCN and formaldehyde in the premix to form glycolonitrile is avoided by keeping the pH of the premix less than or equal to about 1. The acid stabilized mixture can be prepared by charging warm (approximately 50° C.) $CH_2O$ to a stirred vessel, adding acid such as 93% $H_2SO_4$ or 85% $H_3PO_4$ until a pH of about 1 is obtained, cooling the mixture to about 30° C., and adding the hydrogen cyanide. On a commercial scale, the premix may not be as practical.

Instead, HCN and CH₂O can be kept separate and metered via mass flow meters.

Figure 1A:
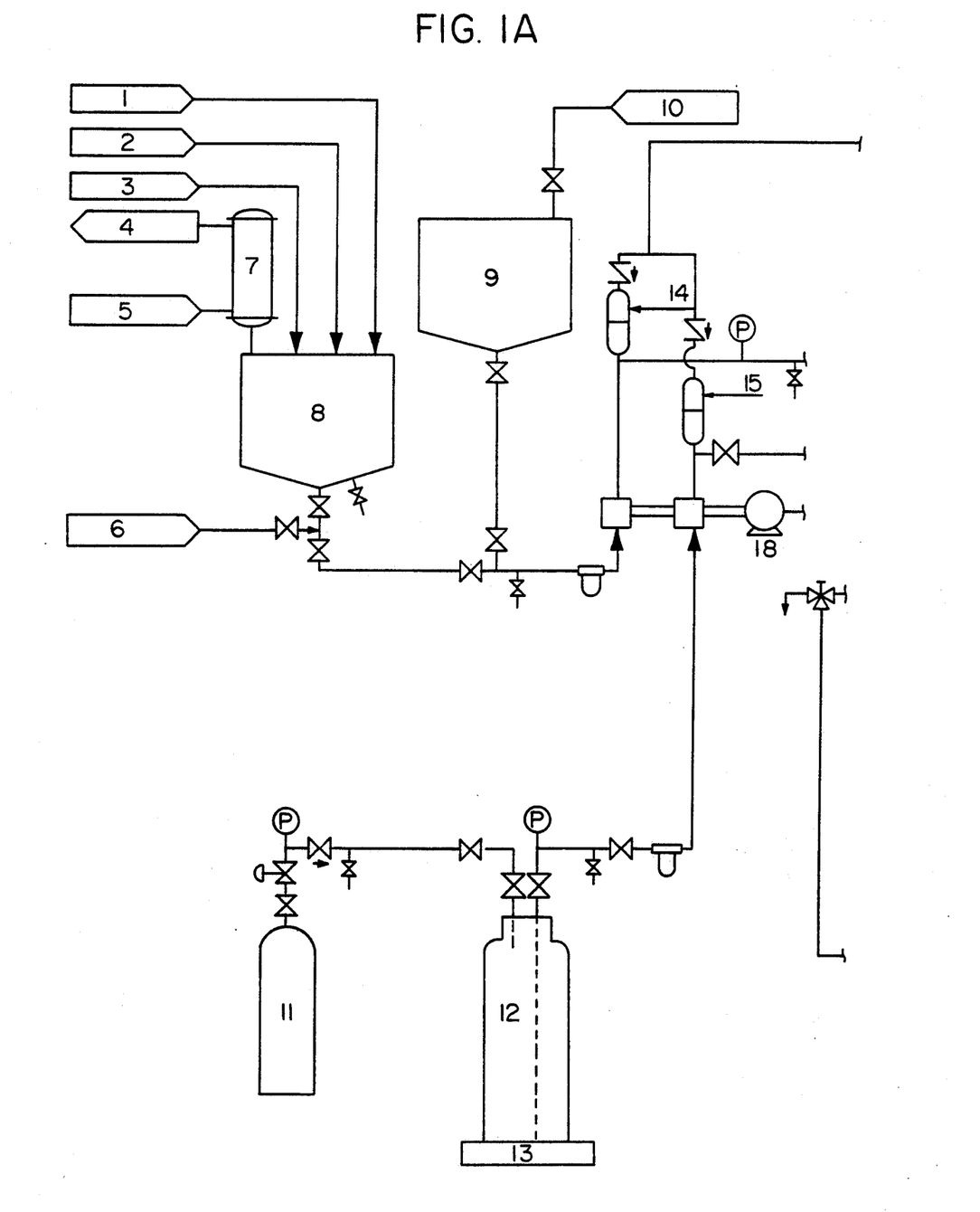
FIGS. 1A-1B-1C are a diagram of an embodiment of the continuous process of the instant invention. The process streams and equipment components of FIGS. 1A-1B-1C are identified in Table III.
Figure 1B:
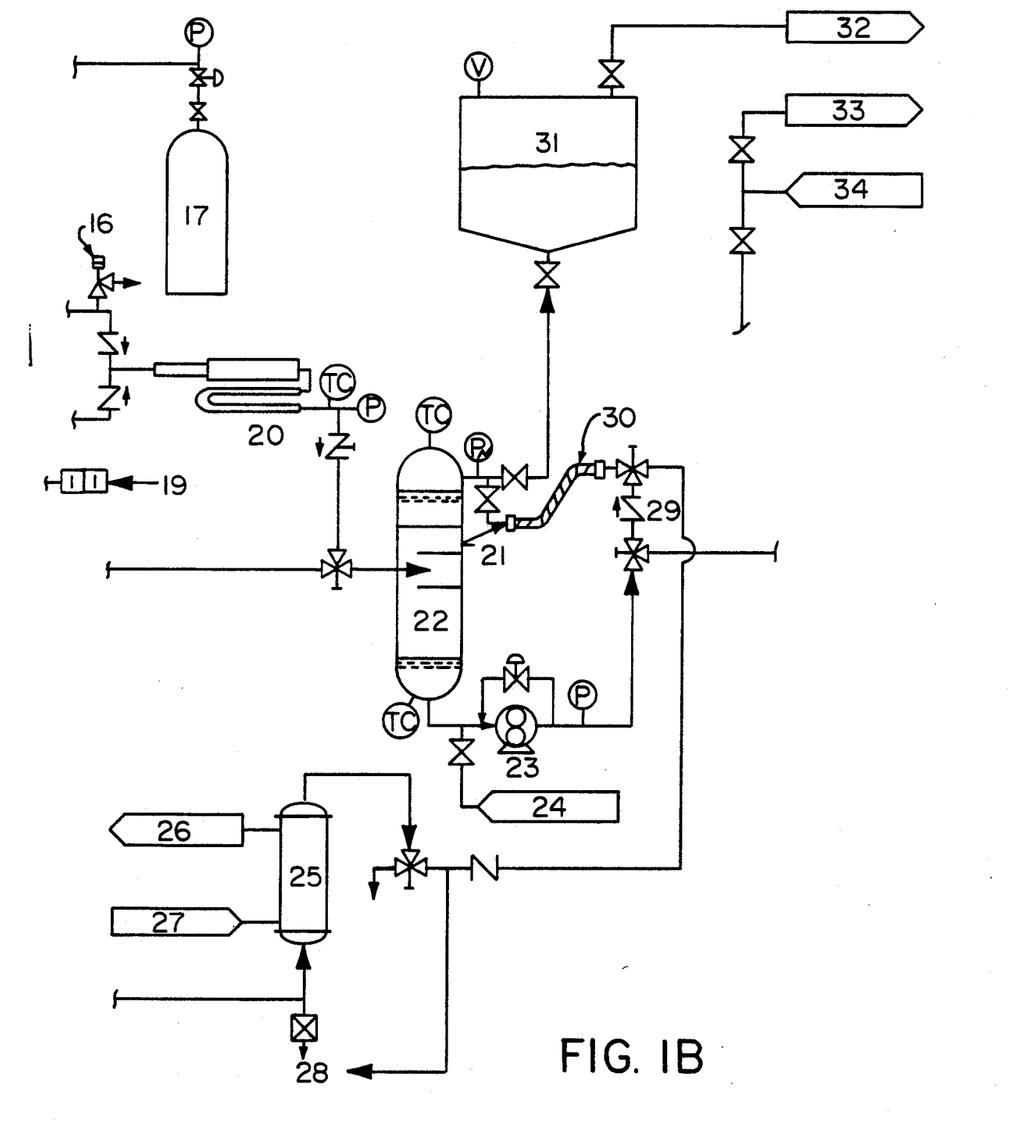
Figure 1C:
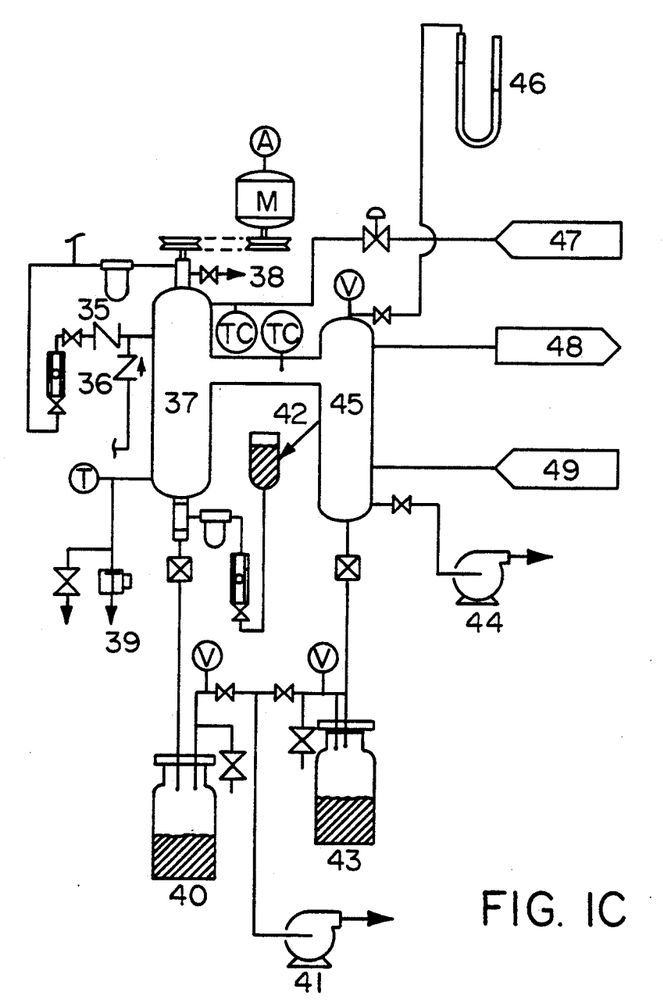

With reference to FIG. 1 and Table III, a continuous tube reactor 20 operating at high pressure and temperature and short residence time is used to prepare crude glycinonitrile solution. The following reactions (not balanced) occur in the tube:

$$HCN + CH_2O \rightarrow OHCH_2CN + 10 Kcal/g\text{-mole} \quad (1)$$

$$OHCH_2CN + NH_3 \rightarrow H_2NCH_2CN + HN(CH_2CN)_2 + H_2O$$

The ammonia concentration should be sufficiently high to allow temperatures greater than about 120° C. to be reached. A suitable ammonia concentration is about 80–100%, with a concentration of about 90–95% being preferred. The amount of ammonia used should be a minimum of about 200% stoichiometric excess.

A suitable reactor for the substantially adiabatic conversion of the feedstock to glycinonitrile is an insulated continuous tube reactor equipped with a back pressure valve. The pressure in the reactor must be adequate to maintain the fluid in the tube in a liquid state. Pressures of 300–400 psig have been found to be operable. Ancillary equipment includes a metering pump 18 equipped with, preferably, diaphragm heads for pumping the ammonia and hydrogen cyanide, and a plunger or diaphragm head for pumping the formaldehyde or the hydrogen cyanide and formaldehyde premix. The pumping rates should be controlled to produce volumetric rates which will maintain a substantially constant molar ratio between the ammonia and the hydrogen cyanide and formaldehyde or the cyanide/formaldehyde mixture and simultaneously give a residence time within the tubular reactor which is just adequate to convert 98–100% of the HCN to nitriles. This molar ratio can vary over a wide range, from a minimum of about 1.5:1 to a practical maximum of 10:1. A preferred range is 3–5:1.

In one embodiment of the present invention, the ammonia and hydrogen cyanide and formaldehyde or the HCN/CH₂O premix enter separate heads of a duplex or triplex metering pump 18 from premix tank 8 in a mole ratio of NH₃:HCN:CH₂O of about 3:1:1.05. The output of each pump enters a mixing tee or cross which is attached directly to the insulated tube reactor. Upon mixing, the heat of reaction causes the temperature of the stream to rise immediately to about 150° C. After a residence time sufficient to carry the reaction to about 98–99% completion, typically about 8–20 seconds, more preferably about 10–16 seconds, the product discharges from the tube through the back pressure valve into a flash tank 22. Since the reaction is carried out adiabatically, the temperature is a function of the mole ratio of reactants, the concentration of ammonia, the residence time, and pressure (when the pressure is less than the vapor pressure of the system). It is preferable that a temperature of about 120°–180° C. be reached, more preferably about 140° C.–180° C., most preferably about 140°–150° C. The aforementioned relatively short residence times are critical, since the rate of decomposition of glycinonitrile is very rapid at these high temperatures.

The flash tank 22 serves several functions; it immediately drops the product temperature by about 100° C., thereby greatly reducing the rate of decomposition of the nitrile; it drops the pressure to about atmospheric, it reduces the vapor load to apparatus downstream, thereby reducing the size of that apparatus, and it produces a vapor rich in ammonia, which, can be absorbed in a scrubber to produce dilute aqueous NH₃, or can be compressed and fed directly to the upper section of an NH₃ still, where water and impurities such as traces of glycinonitrile are removed, whereupon the ammonia can be recycled. Alternatively, the concentrated ammonia vapor could be fed to a chilled water scrubber to directly produce aqueous ammonia at the commercial concentration of 28%. A suitable flash tank includes a large diameter pipe and flanges and is equipped with a demister pad in the upper section.

In the flash tank 22, most of the ammonia and some of the water flash to vapor through the demister in the top of the tank, and the product, water, and non-volatile by-products collect in the bottom as a liquid at a temperature of about 70° C.

A gear pump 23 can be used to transfer the liquid collected in the bottom of the flash tank to a wiped film evaporator 37 operated at about 20 mm Hg and equipped with a jacket through which steam is supplied at a pressure of about 40–60 psig. Preferably the steam is at a temperature of about 150° C.–180° C., most preferably about 180° C. A retaining ring or dam can be used at the base of the stripper to increase retention of the tars in order to give better recovery of distillate.

The volatile product, water, and residual ammonia from the evaporator 37, are distilled into a condenser 45 and collected. The non-volatile by-products collect at the bottom of the evaporator where they are removed as a waste stream 40 or can be further processed for recovery of IDAN, as discussed hereinbelow. If the distilled glycinonitrile contains a small amount of IDAN (such as from entrainment of droplets of undistilled material in the distillate) and such is undesirable, a vapor-liquor separator can be used between the stripper and the condenser.

The resulting distilled product can be saponified with a base, such as 30% NaOH or KOH, and sent to a crystallizer or spray dryer for recovery of the alkali metal glycinate. Alternatively, or in addition, the alkali metal glycinate can be converted to glycine acid by several different processes known to those skilled in the art, including ion-exchange, electrodialysis, electrolysis, and fractional crystallization as described in U.S. Pat. No. 3,904,585, the disclosure of which is herein incorporated by reference. The resulting alkali metal glycinate and glycine derived therefrom contain considerably less impurities, such as iminodiacetic acid (IDA), than that produced by conventional processes.

The main constituent of the bottoms from the stripper is IDAN. By dilution with water and subsequent crystallization, crude, relatively pure IDAN can be isolated. The liquor can be saponified in alkali metal hydroxide to produce a solution containing primarily alkali metal iminodiacetate and glycinate, which could be converted to a zinc chelate, for example. As a result, most of the stripper bottoms effluent, which might otherwise be considered a waste stream, can be converted into useful products.

In the following examples, glycinonitrile was synthesized and distilled by an integrated continuous process in the pilot apparatus shown in FIG. 1. The most important components of that apparatus were:

Duplex metering pump 18: Lewa model HUM-1/HU-1 equipped with a M114 diaphragm head for anhydrous ammonia and a K101.1 plunger head for pumping HCN/CH$_2$O premix. Pulsation dampers 14, 15 were mounted on the outlet of each pump head. The motor speed was controlled with an inverter motor speed control 19.

Tube Reactor: The reactor 20 was constructed from standard components assembled in the following order: a $\frac{1}{4} \times 7''$ Kinecs static mixer, a segment of $\frac{3}{8}''$ o.d. stainless steel tubing of variable length as needed to produce a range of residence times, and a Tescom model 26-1726-25-043 backpressure/relief valve. The entire reactor was insulated.

Flash Tank: Flash tank 22 was assembled from a 4" Pyrex pipe Tee, two 4"×1" Pyrex reducers, and flanges. The upper section above the point of entry of the hot glycinonitrile solution from the tube reactor, was filled with a stainless steel 4"×4" "Mister-Mesh" demister pad, style no. 4BA.

Wiped Film Evaporator/Condenser Package: This unit was a Luwa "Pilot Plant Package B" consisting of a Luwa Thin Film Evaporator 37 Model LN-0012 (1.4 ft$^2$ heat exchange surface) connected through a 3" vapor pipe to an American Standard Model SSCF06024 stainless steel condenser 45 (23 ft$^2$ heat exchange area).

The feedstocks were technical concentrated NH$_3$ with an average NH$_3$ content of 92%, and an aqueous solution of HCN and 44% CH$_2$O stabilized with sulfuric acid to pH $\leq$1.0. Hereafter, this solution is called "Pre-Mix". The preparation is described in Example 1. Nitrogen pressure was added to the NH$_3$ supply cylinder to maintain constant pressure throughout a run, since as the liquid NH$_3$ level dropped as it was being used, the pressure would drop, thereby changing the pumping rate, and hence the mole ratio to the pre-mix and the residence time, since the total volume being pumped would change. Nitrogen pressure need not be used where constant pressure NH$_3$ is available. Table III lists the numbers and elements depicted in FIG. 1.

EXAMPLE 1

Pre-Mix was prepared in a 30 gallon stainless steel reactor 8. To the reactor from line 1 was charged 154.4 lb (1.51 lb moles) of 44.0% CH$_2$O and from line 3, 0.2 lb (0.3 lb moles) of 50% H$_2$SO$_4$. This solution was cooled to 25°–30° C., then 60.0 lb (1.48 lb moles) of HCN was added from line 2. This solution was maintained at 10°–20° C.

A section of $\frac{3}{8}''$ o.d. stainless steel tubing sufficient to give a total internal tube reactor 20 volume of 134 ml was added to the reactor. The Pre-Mix pump rate was adjusted by pumping and weighing the water exiting the reactor. Then pumping of NH$_3$ from supply 12 was started and the rate was adjusted, again by weighing the output from the reactor. Once calibration was completed, the feed to the Pre-Mix pump head was switched from water to Pre-Mix, then further adjustment of the Pre-Mix rate was made if necessary to give a mole ratio of NH$_3$:HCN of close to 3.0:1. The tube reactor pressure throughout calibration and reaction was maintained at a nominal 300 psig. The product was sampled and analyzed for total non-reacted cyanide by titration with standard silver nitrate in an alkaline solution. From this analysis and the known pumping rates of the reactants, the % conversion (% reaction) of HCN to nitriles was calculated. The rpm of the motor was then adjusted with inverter 19 to change the total flow rate to the reactor, and hence the residence time in the reactor, to a time just adequate to give 98.5–99.5% reaction.

Once these adjustments were finished, the hot glycinonitrile solution exiting the reactor was diverted to the flask tank 22. The NH$_3$/water vapor from the top of the flash tank was vented to a water scrubber 31. The bottoms in the flash tank contained the glycinonitrile, organic impurities (primarily iminodiacetonitrile), water, and some NH$_3$. Once several inches of bottoms had accumulated, gear pump 23 used to transfer the bottoms to the stripper 37 was started. While diverting the flow to waste, the pumping rate was adjusted to a rate that would give a constant level in the bottom of the flash tank.

Once all these adjustments were made, operation of the wiped film evaporator began. The rotor was started, vacuum was applied via vacuum pump 44 to the evaporator and to the sampling containers at the outlet of the condenser and at the bottom of the evaporator. Steam flow to the evaporator jacket and chilled brine flow 49 to the jacket of the condenser 45 were then started. Then, the injection of product from the flash tank bottoms into the evaporator via the gear pump began. After all flow rates and temperatures were equilibrated, the collection containers at the bottom of the evaporator and condenser were switched for new, empty containers, and product 43 (from the condenser) and nonvolatile residue 40 (from the evaporator) were collected for a timed interval. With these data, the rates and efficiency of evaporation could later be calculated. The product collected was later analyzed for glycinonitrile (GN), iminodiacetonitrile (IDAN), water, and ammonia.

When the first set of samples from the evaporator had been taken, the steam pressure to the evaporator jacket was increased and the process of evaporator equilibration and sampling was repeated. In this way, pairs of samples of condensed evaporator distillate (Product) and bottoms (residue) were obtained with jacket steam temperatures of 150° C., 160° C., 170° C., and 180° C. The results are summarized in Table I.

EXAMPLE 2

The section of $\frac{3}{8}''$ stainless steel tubing was removed from the tube reactor and was replaced with a longer segment which gave a total reactor volume of 189 ml. The procedure of Example 1 was repeated at increased flow rates to the reactor. The evaporator was operated at steam jacket temperatures of 158° C. and 170° C. The results are summarized in Table I.

EXAMPLE 3

The internal volume of the tube reactor was increased to 238 ml and the procedure of Example 1 was repeated at increased flow rates to the reactor. The evaporator was operated at jacket steam temperatures of 160° C., 170° C., and 182° C. The results are summarized in Table I.

EXAMPLE 4

The internal volume of the tube reactor was reduced to 88.5 ml and the procedure of Example 1 was repeated at decreased flow rates to the reactor. The relative Pre-Mix and NH$_3$ feed rates were adjusted to give an NH$_3$ HCN mole ratio of 2.56:1. The evaporator jacket steam temperatures were 155° C., 165° C., and 175° C. The results are summarized in Table I.

EXAMPLE 5

The procedure and reactor configuration of Example 4 was repeated but at an $NH_3$:HCN mole ratio of 2.95:1. The entire system was operated for one hour using 140° C. evaporator jacket steam temperature. All condensed distillate was immediately chilled and saved. All residue from the bottom of the evaporator was also saved. The results are summarized in Table I.

The total flow rates from the tube reactor in the preceding examples were over a range of 301–885 g/min. The mole ratio of $NH_3$:(HCN and $CH_2O$) was near 3:1 in Examples 1, 2, 3, and 5. For those runs, the yield of glycinonitrile from HCN was 90.8±1.6%. That mole ratio in Example 4 was about 2.6:1. The yield from that run was 85.9%. This illustrates the significant impact of mole ratio upon yield.

These data also show that consistent yields are attained over a wide range of flow rates, provided that the $NH_3$:(HCN and $CH_2O$) mole ratio is carefully controlled and that the residence time/temperature relationships are balanced in such a way as to give 98–99% conversion of HCN to nitriles. Whenever the residence time or temperature, or both, were increased in an attempt to drive the reaction to 100%, the product was black and contained particulate matter which plugged the equipment; therefore, no useful data could be obtained for those conditions.

TABLE I
GLYCINONITRILE EXAMPLES
SUMMARY OF GLYCINONITRILE PREPARATION AND DISTILLATION EXAMPLES

|  | EXAMPLE 1 | | | | EXAMPLE 2 | | | EXAMPLE 3 | |
|---|---|---|---|---|---|---|---|---|---|
| Reactor/Flash Tank Data | | | | | | | | | |
| Tube Reactor Internal Volume, ml | 134 | | | | 189 | | | 238 | |
| % HCN in Total Feed to Reactor | 17.9% | | | | 18.0% | | | 17.6% | |
| Mole Ratio NH3:1.00 HCN in Reactor Feed | 2.91 | | | | 2.88 | | | 3.07 | |
| Residence Time in Reactor, seconds | 12.3 | | | | 15.8 | | | 16.1 | |
| Product Exiting Reactor: % Reaction | 98.6% | | | | 98.9% | | | 99.6% | |
| g/min | 652 | | | | 717 | | | 885 | |
| Product Collected in Flash Tank Bottoms: | | | | | | | | | |
| g/min | 482 | | | | 553 | | | 704 | |
| % GN | 46.2% | | | | 43.1% | | | 42.4% | |
| % IDAN | | | | | | | | | |
| % NH3 | 4.8% | | | | 5.4% | | | 4.7% | |
| Temperature, °C.: Reactor, Before Relief Valve | 157° C. | | | | 150° C. | | | | |
| Flash Tank Bottoms | 68° C. | | | | 63° C. | | | 68° C. | |
| Flash Tank Vapors | 67° C. | | | | 63° C. | | | 56° C. | |
| % Yield of GN in Flash Tank Bottoms from HCN | 91.9% | | | | 88.9% | | | 92.4% | |
| Evaporator Data | | | | | | | | | |
| Steam Temperature to Evaporator Jacket, °C. | 150° C. | 160° C. | 170° C. | 180° C. | 158° C. | 170° C. | 160° C. | 170° C. | 182° C. |
| Pressure, mm Hg | | | | | 26 | 27 | 29 | 38 | 29 |
| Flow Rates, g/min | | | | | | | | | |
| Feed to Evaporator | 482 | 482 | 482 | 482 | 583 | 583 | 704 | 704 | 704 |
| Distillate | 429 | 434 | 433 | 436 | 481 | 497 | 630 | 639 | 637 |
| Bottoms | 28.3 | 27.5 | 24.3 | 20.3 | 34.3 | 28.0 | 40.4 | 31.6 | 26.8 |
| Analysis of Feed | | | | | | | | | |
| % GN | 46.2% | 46.2% | 46.2% | 46.2% | 43.1% | 43.1% | 42.4% | 42.4% | 42.4% |
| % IDAN | | | | | | | | | |
| % NH3 | 4.8% | 4.8% | 4.8% | 4.8% | 5.4% | 5.4% | 4.7% | 4.7% | 4.7% |
| Analysis of Distillate | | | | | | | | | |
| % GN | 48.2% | 49.3% | 49.2% | 49.7% | 44.5% | 45.0% | 44.1% | 44.1% | 44.3% |
| % IDAN | | | | | | | | | |
| % NH3 | 1.4% | 1.7% | 1.7% | 1.7% | 2.1% | 2.1% | 2.3% | 2.2% | 2.4% |
| Analysis of Bottoms | | | | | | | | | |
| % GN | 19.6% | 22.5% | 23.4% | 22.5% | 33.1% | 28.3% | 24.1% | 25.5% | 26.0% |
| % IDAN | | | | | | | | | |
| % NH3 | 0.0% | 0.0% | 0.0% | 0.0% | 0.0% | 0.0% | 8.7% | 5.8% | 5.0% |
| % of GN in Feed Recovered in Distillate | 92.9% | 96.0% | 95.7% | 97.2% | 89.9% | 93.9% | 94.5% | 95.4% | 97.5% |
| % Yield of Distilled GN from HCN | 85.4% | 88.2% | 88.0% | 89.4% | 79.9% | 83.5% | 90.9% | 90.9% | 92.9% |

|  | EXAMPLE 4 | | | EXAMPLE 5 |
|---|---|---|---|---|
| Reactor/Flash Tank Data | | | | |
| Tube Reactor Internal Volume, ml | 88.5 | | | 88.5 |
| % HCN in Total Feed to Reactor | 18.9% | | | 18.0% |
| Mole Ratio NH3:1.00 HCN in Reactor Feed | 2.56 | | | 2.95 |
| Residence Time in Reactor, seconds | 17.1 | | | 12.5 |
| Product Exiting Reactor: % Reaction | 98.5% | | | 98.8% |
| g/min | 307 | | | 301 |
| Product Collected in Flash Tank Bottoms: | | | | |
| g/min | 237 | | | 232 |
| % GN | 43.4% | | | 43.8% |
| % IDAN | 6.0% | | | 4.9% |
| % NH3 | 4.2% | | | 5.2% |
| Temperature, °C.: Reactor, Before Relief Valve | 165° C. | | | |
| Flash Tank Bottoms | 75° C. | | | |
| Flash Tank Vapors | 68° C. | | | |
| % Yield of GN in Flash Tank Bottoms from HCN | 85.9% | | | 90.0% |
| Evaporator Data | | | | |
| Steam Temperature to Evaporator Jacket, °C. | 155° C. | 165° C. | 175° C. | 140° C. |
| Pressure, mm Hg | | | | 38 |

TABLE I-continued
GLYCINONITRILE EXAMPLES
SUMMARY OF GLYCINONITRILE PREPARATION AND DISTILLATION EXAMPLES

| Flow Rates, g/min | | | | |
|---|---|---|---|---|
| Feed to Evaporator | 240 | 240 | 240 | 232 |
| Distillate | 204 | 213 | 211 | 207 |
| Bottoms | 34.0 | 21.0 | 32.0 | 17.5 |
| Analysis of Feed | | | | |
| % GN | 43.4% | 43.4% | 43.4% | 43.8% |
| % IDAN | 6.0% | 6.0% | 6.0% | 4.9% |
| % NH3 | 4.2% | 4.2% | 4.2% | 5.2% |
| Analysis of Distillate | | | | |
| % GN | 42.3% | 44.3% | 42.1% | 47.5% |
| % IDAN | 1.1% | 3.0% | 1.1% | 0.3% |
| % NH3 | 3.4% | 1.7% | 4.7% | 1.8% |
| Analysis of Bottoms | | | | |
| % GN | 34.3% | 29.5% | 26.3% | 20.9% |
| % IDAN | | | | 47.2% |
| % NH3 | 0.0% | 0.0% | 0.0% | 0.0% |
| % of GN in Feed Recovered in Distillate | 83.0% | 90.8% | 85.4% | 96.7% |
| % Yield of Distilled GN from HCN | 71.2% | 78.1% | 73.5% | 87.1% |

The following data extracted from Table 1 are useful in illustrating the performance of the wiped film evaporator.

| Example | Feed Rate To Evaporator g/min | Jacket Temp °C. | % NH3 in Evaporator Bottoms | % of the GN in the Feed Recovered as Distillate |
|---|---|---|---|---|
| 1 | 482 | 150 | 0.0% | 92.9% |
| | | 160 | 0.0% | 96.0% |
| | | 170 | 0.0% | 95.7% |
| | | 180 | 0.0% | 97.2% |
| 2 | 583 | 158 | 0.0% | 89.9% |
| | | 170 | 0.0% | 93.9% |
| 3 | 704 | 160 | 8.7% | 94.5% |
| | | 170 | 5.8% | 95.4% |
| | | 182 | 5.0% | 97.5% |

COMPARISON OF EVAPORATION DATA FROM EXAMPLES 1 to 5

From Examples 1 through 3, the feed rate to the stripper was increased from 482 to 583 to 704 g/min. NH3 was totally removed from the bottoms under all conditions in the first two examples, but not at the fastest feed rate used; i.e., Example 3.

In Examples 1 and 3 it can be seen that by increasing the jacket temperature, the recovery of distilled glycinonitrile can be increased to near 98%.

EXAMPLE 6

All distilled glycinonitrile recovered from Example 5 was base-hydrolyzed in NaOH to produce a solution of sodium glycinate. 12.4 kg of glycinonitrile solution (approximate composition, 47.5% GN) was slowly added to 15.4 kg of 30% NaOH at a temperature of about 70° C. This solution was boiled until free of NH3, cooled to 80° C., and bleached with 100 g of 50% H2O2. 20.7 kg of Na glycinate solution containing 41% Na glycinate and 0.73% iminodiacetic acid (IDA) (expressed as the free acid) was produced.

EXAMPLE 7

1049 g of stripper bottoms recovered from Example 5 was diluted with 630 g of water and cooled to produce a slurry of IDAN. This slurry was filtered and washed. 407 g of light tan colored IDAN crystals (97.7%, as determined by HPLC), were recovered. Thus, 82% of the IDAN in the stripper bottoms was recovered as a crystalline powder.

EXAMPLE 8

Glycine and sodium sulfate were recovered from the sodium glycinate solution produced in Example 6 by the fractional crystallization procedure described in U.S. Pat. No. 3,904,585. The original pair of fractional crystallizations followed by 14 cycles including recycle of all mother liquor were completed before the experiment was terminated.

Sodium Sulfate Separation: In a 2 liter stainless steel beaker, 1000 g of Na glycinate (41.0%) was diluted with water to 27% sodium glycinate. All mother liquor recovered from a previous cycle (except for the first crystallization of the series) was added. The pH of this solution was reduced to 6.0 by the addition of 50% $H_2SO_4$ while cooling to keep the temperature $\leq 60°$ C. This solution was boiled until a moderately heavy $Na_2SO_4$ slurry was present. This hot slurry was transferred to a 1L graduate to measure the volume of settled crystals. The slurry was returned to the beaker and boiling was continued until the volume percent crystals was 20%. This hot slurry (>80° C.) was fed to a pre-heated centrifuge to separate the crystallized $Na_2SO_4$. The $Na_2SO_4$ cake was not washed before being dried.

Glycine Separation: The hot liquor was reheated to 90° C. and crystallized by cooling to 35° C. over 90 minutes using a non-linear cooling curve which was uniform for all glycine crystallizations. The slurry was centrifuged in a warmed centrifuge. The crystals were washed with about 10 ml of water. (This amount of water was sufficient to displace only a portion of the mother liquor adhering to the glycine crystals. No attempt was made in these experiments to produce a product free of sodium sulfate.) A 10–15g sample of mother liquor was taken before addition of wash water for later analysis. The remaining liquor plus wash was recycled to the next crystallization cycle. This process was repeated for 15 cycles. No deterioration of crystallinity of $Na_2SO_4$ or glycine, no problem of solid/liquid separation, and no significant increase in the color of the liquor was observed in any of these cycles. The results of these crystallizations are summarized in Table II.

TABLE II

GN Patent - Frac. Xtlzn.
SUMMARY OF GLYCINE/SODIUM SULFATE FRACTIONAL CRYSTALLIZATION CYCLES

| | CHARGED | | | GLYCINE RECOVERED | | | | | |
|---|---|---|---|---|---|---|---|---|---|
| CYCLE NO. | Fresh 41.0% Na Glycinate, grams | Recycled Liquor, grams | Cumulative Glycine, grams | Glycine Crop, Partially Washed, Dried | | | | Cumulative g Glycine | Cumulative Glycine Yield |
| | | | | Grams | % Glycine | % Na2SO4 | % IDAH2 | | |
| 1 | 1000 | 0 | 317 | 311 | 75.4% | 26.4% | 0.2% | 234 | 73.9% |
| 2 | 1000 | 400 | 634 | 289 | 83.9% | 14.0% | 0.3% | 477 | 75.2% |
| 3 | 1000 | 653 | 951 | 346 | 86.6% | 12.8% | 0.3% | 777 | 81.6% |
| 4 | 1000 | 844 | 1268 | 386 | 84.2% | 17.0% | 0.4% | 1102 | 86.9% |
| 5 | 1000 | 759 | 1586 | 398 | 82.5% | 18.6% | 0.4% | 1430 | 90.2% |
| 6 | 1000 | 634 | 1903 | 322 | 86.5% | 9.5% | 0.3% | 1708 | 89.8% |
| 7 | 1000 | 844 | 2220 | 313 | 94.2% | 6.6% | 0.3% | 2003 | 90.3% |
| 8 | 1000 | 923 | 2537 | 271 | 89.5% | 12.0% | 0.6% | 2246 | 88.5% |
| 9 | 1000 | 727 | 2854 | 256 | 96.7% | | 0.5% | 2493 | 87.4% |
| 10 | 1000 | 1162 | 3171 | 406 | 87.5% | 10.2% | 0.4% | 2849 | 89.8% |
| 11 | 1000 | 1142 | 3488 | 377 | 88.8% | 10.2% | 0.5% | 3183 | 91.3% |
| 12 | 1000 | 1072 | 3805 | 377 | 85.6% | 13.9% | 0.4% | 3506 | 92.1% |
| 13 | 1000 | 911 | 4122 | 411 | 87.6% | 12.8% | 0.7% | 3866 | 93.8% |
| 14 | 1000 | 762 | 4439 | 340 | 86.9% | 13.8% | 0.9% | 4162 | 93.7% |
| 15 | 1000 | 666 | 4757 | 317 | 85.0% | 15.4% | 0.4% | 4431 | 93.2% |

TABLE III

1. Formaldehyde Feed
2. Hydrogen Cyanide Feed
3. Acid Feed
4. Brine Return
5. Brine Supply
6. Water Line
7. Heat Exchanger
8. Premix Tank
9. Water Tank
10. Water Line
11. Nitrogen Supply
12. Ammonia Supply
13. Scale
14. Damper
15. Damper
16. Pressure Relief Valve Set at 400 p.s.i.
17. Nitrogen Supply
18. Metering Pump
19. Inverter Motor Speed Control
20. Reactor
21. Air Bleed (When Hose is Disconnected)
22. Flash Tank
23. Gear Pump
24. Water Line
25. Heat Exchanger
26. Brine Return
27. Brine Supply
28. Waste Line
29. Back Pressure Check Valve at 5-10 p.s.i.
30. Hose
31. Scrubber Tank
32. Line to Vacuum System
33. Water Line Flush
34. Water Supply
35. Back Pressure Check Valve at 20 p.s.i.
36. Back Pressure Check Valve at 20 p.s.i.
37. Thin Film Stripper
38. Line to Waste
39. Steam Trap
40. Waste
41. Vacuum Pump
42. Glycerine/H2O lubricant fed to lower bearing
43. Product
44. Vacuum Pump
45. Heat Exchanger
46. Mercury Manometer
47. Steam Supply
48. Brine Return
49. Brine Supply LEGEND
SHUTOFF VALVE
ADJUSTABLE BACK PRESSURE CHECK VALVE
BALL VALVE
THREE WAY VALVE
PRESSURE RELIEF VALVE

TABLE III-continued

PRESSURE REGULATING VALVE
N BACK PRESSURE CHECK VALVE
FILTER
ADJUSTABLE FLOW METER
STEAM TRAP
P PRESSURE GAGE
PRESSURE VACUUM GAGE
V VACUUM GAGE
T TEMP. GAGE
0 THERMOCOUPU
A

What is claimed is:

1. A continuous process for preparing glycinonitrile which comprises:
   combining hydrogen cyanide, formaldehyde, and ammonia to attain a reaction;
   maintaining said reaction under substantially adiabatic reaction conditions and at a substantially constant ammonia to formaldehyde and cyanide mole ratio of about 1.5:1 to about 10:1, a temperature from about 120° C. to about 180° C., and a pressure sufficient to maintain the reactants in a liquid state, and recovering glycinonitrile from the reaction mixture.

2. The process according to claim 1 wherein the ammonia source is about 80-100% ammonia.

3. The process of claim 1 wherein the ammonia source is about 90-95% ammonia.

4. The process of claim 1 wherein the reactants react to produce a temperature of about 140°-150° C.

5. The process of claim 1 wherein the reaction is accomplished by reactively contacting the ammonia with a premix of formaldehyde and hydrogen cyanide.

6. The process of claim 5 wherein said premix is acid stabilized.

7. The process of claim 1 wherein said pressure is about 300-400 psig.

8. The process of claim 1 wherein the residence time of the reactants is about 8-20 seconds.

9. The process of claim 1 wherein said recovery of glycinonitrile comprises flashing ammonia from the reaction mixture and separating and recovering glycinonitrile from the remaining liquid.

10. The process of claim 9 wherein the separation step comprises subjecting said remaining liquid to evaporation followed by condensation of the remaining vapors.

11. A process for preparing alkali metal glycinate which comprises:
(a) bringing into reactive contact hydrogen cyanide, formaldehyde and ammonia in an ammonia to formaldehyde and hydrogen cyanide mole ratio of about 1.5:1 to about 10:1, a temperature from about 120° C. to about 180° C., and a pressure sufficient to maintain the reactants in a liquid state;
(b) maintaining the reaction under substantially adiabatic conditions;
(c) flashing ammonia from the resulting reaction mixture;
(d) evaporating remaining volatile liquor and condensing the resulting vapors;
(e) saponifying the condensate with alkali metal hydroxide to form said alkali metal glycinate.

12. The process of claim 11 wherein said alkali metal glycinate is sodium glycinate.

13. The process of claim 11 wherein said alkali metal glycinate is potassium glycinate.

14. The process according to claim 1 wherein the reaction is carried out in a tubular reactor.

15. The reaction according to claim 11 wherein the reaction is carried out in a tubular reactor.

* * * * *